US006362224B2

(12) United States Patent
Renello

(10) Patent No.: US 6,362,224 B2
(45) Date of Patent: Mar. 26, 2002

(54) ENHANCED TERMITICIDE AND METHOD FOR TREATING TERMITES

(76) Inventor: Leo A. Renello, 8540 E. McDonnell Rd., Mesa, AZ (US) 85207

( * ) Notice: Subject to any disclaimer, the term of this patent is extended or adjusted under 35 U.S.C. 154(b) by 0 days.

(21) Appl. No.: 09/757,199

(22) Filed: Jan. 9, 2001

Related U.S. Application Data

(63) Continuation-in-part of application No. 08/832,068, filed on Apr. 2, 1997, now Pat. No. 6,172,051.

(51) Int. Cl.⁷ .................. A01N 37/34; A01N 53/00; A01N 25/00
(52) U.S. Cl. ................ 514/521; 514/531; 424/84
(58) Field of Search ................... 514/521, 531; 424/84

(56) References Cited

U.S. PATENT DOCUMENTS

| | | | |
|---|---|---|---|
| 3,858,346 A | 1/1975 | Bailey | 43/124 |
| 4,310,520 A | 1/1982 | Narazaki | 424/200 |
| 4,582,901 A | 4/1986 | Prestwich | 536/83 |
| 4,849,415 A | 7/1989 | Zwergle | 514/89 |
| 5,564,222 A | 10/1996 | Brody | 43/124 |
| 5,573,760 A | 11/1996 | Thorne et al. | 424/84 |

*Primary Examiner*—Allen J. Robinson
(74) *Attorney, Agent, or Firm*—Joseph W Mott

(57) ABSTRACT

An improved termiticidal combination is formed by adding a liquid cellulose source to a standard liquid termiticide. The cellulose source may be a water soluble polyester such as a cellulose ether like methyl cellulose. The cellulose in the combination functions as termite bait, thereby enhancing the effectiveness of the poison, even at lower concentrations, by inducing termites to ingest poisoned cellulose and return with it to share it with the colony. The liquid form allows the combination to be applied with a standard power sprayer, and permits laying of a continuous barrier or curtain as well as injection spraying into walls of structures.

11 Claims, No Drawings

ENHANCED TERMITICIDE AND METHOD FOR TREATING TERMITES

This application is a continuation-in-part of application Ser. No. 08/832,068, filed Apr. 2, 1997, now U.S. Pat. No. 6,172,051, the disclosure of which is incorporated herein by reference.

FIELD OF THE INVENTION

The invention relates to the field of pesticides in general and more specifically to termiticides.

BACKGROUND OF THE INVENTION

Subterranean termites present a serious threat to structures, and particularly residential structures, throughout most of the United States and in many parts of the world. One of the most widely used techniques to combat termite infestation is the application of chemical agents to the ground under and around the structure. In a typical preconstruction treatment situation, a liquid form termiticide is sprayed at specified concentrations and volumes directly onto the compacted soil immediately before the concrete slab is poured, creating a horizontal barrier between any subterranean nests and the underside of the slab. Additional barriers are created in by boring holes into the soil at specified intervals (often 18 inches) or by digging trenches around the structure and spraying termiticide into the openings as well as mixing termiticide with the backfill soil. If treatment is required to control active infestation that occurs after construction, techniques include drilling holes in infested walls and injecting liquid or powdered termiticides between the walls, boring holes in the floor slab at spaced intervals and injecting liquid termiticides into the soil, and trenching around the base of the structure and applying termiticides as in pretreatment.

In the past, conventional insecticides such as the chlorinated hydrocarbons known as chlordane, DDT, aldrin, dieldrin and BHC could be effectively used to poison the soil so that transiting termites would be killed. These chemicals also remained effective in the ground for many years. Unfortunately, their effectiveness as poisoning agents extended beyond the targeted pests, and environmental concerns have resulted in prohibition of the use of any of these agents for termite treatment. Chlordane was the last such chemical available for either home or professional use, and that was banned by the United States Environmental Protection Agency in 1987.

The pest control industry has been forced to adopt a less potent class of chemical poisons for termite pre-treatment and infestation interdiction. Currently approved by the Environmental Protection Agency are chlorpyrifos (sold under the name DURSBAN TC), cypermethrin (sold as DEMON TC), fenvalerate (sold as TRIBUTE), and permethrin (sold as DRAGNET and as PRELUDE). These chemicals are generally applied in the same manner as their predecessor chlorinated hydrocarbons, namely, spraying beneath a slab or other foundation to form a horizontal barrier and injection through holes or a trench to form a vertical barrier or "curtain" through which terminates cannot penetrate without being killed. They are also used for infestation control. Unfortunately, the very characteristics that make them acceptable from an environmental standpoint (low toxicity and eventual degrading into non-toxic components) render them less effective in long term termite control.

One of the most common termiticides, and the only one available to consumers who are not licensed pest control operators, is chlorpyrifos, an organophosphate that is available in emulsifiable concentrate, dust, flowable, pellet, spray, granular and wettable powder formulations. The chemical adsorbs well to soil particles, is not readily soluble in water, and has a half life of 2 weeks to a year, but most commonly 60 to 120 days. Chlorpyrifos acts as a cholinesterase inhibitor, interfering with the proper working of the nervous system. It works as a contact poison, but also as a stomach poison. A conventional termite barrier laid down by spraying chlorpyrifos is expected to kill termites that pass through it, and to generate secondary kills in the nest when the carcasses of poisoned termites are carried to the nest and cannibalized. The half life virtually assures that the efficacy of the chemical will end before that of the structure. Based on findings of a study of the residual effects of chlorpyrifos on the human nervous system and a revised risk assessment, the Environmental Protection Agency in 2000 banned use of the chemical in post-construction infestation control and dramatically reduced the allowable concentrations in residential pre-treatment, with a 4-year program to phase out chlorpyrifos altogether.

To enhance the effectiveness of termiticidal compounds, both before and after the banning of chlorinated hydrocarbons, the chemicals were combined into termite "baits" consisting of the poison and an attractive termite food, namely, some form of cellulose. The objective is to induce the termites to ingest the poisoned food and return with it to the nest, where food is normally regurgitated and shared with the rest of the colony. Two early examples are U.S. Pat. No. 3,858,346 (Bailey) and U.S. Pat. No. 4,582,901 (Prestwich). Bailey disclosed impregnation of building timbers with hexachlorocyclopentadiene dimer in an organic solvent such as benzene or carbon tetrachloride as the termiticide, and also spreading bait comprising the same poison added to a termite-attracting carbohydrate carrier such as citrus pulp, sawdust and decaying wood. Prestwich discloses modifying the chemical composition of cellulose to include fluorinated ester moieties. The modified cellulose may be formed into bait blocks or injectable dust for placement in areas to be protected or treated.

In more recent, environmentally safer approaches, U.S. Pat. No. 5,564,222 (Brody) discloses impregnating cellulose items, such as wooden or cardboard stakes, balls or pellets with a water soluble borate salt. The termites are attracted to and consume the cellulose and the borate salt functions as a slow-acting termiticide. U.S. Pat. No. 5,573,760 (Thome, et al.) discloses using a termite monitor in the form of a perforated cartridge containing a cellulose-rich composition, water and an exogenous nitrogen source. Once foraging termites encounter the desirable food source, they recruit others, and a tunnel to the device is constructed. This, allows early detection of termites near a protected structure, as the bait is a more desirable food than the structure. Once activity is identified, the cartridge can be removed and replaced with a similar cartridge containing the same food composition, but laced with a slow-acting termiticide.

The bait approach as previously implemented has at least two disadvantages. First, there are necessarily gaps between the bait modules, leaving the possibility that termites may simply miss; the bait, tunneling between the modules and reaching and infesting the protected structure. Current protection standards require a horizontal barrier and vertical curtain without any gaps. Second, placing of the bait modules, whether spikes, buried balls, pellets or dust., is time consuming, labor intensive and consequently expensive. The closer together the bait modules, the more work and expense involved.

In a generalized application not directed to the control of termites, U.S. Pat. No. 4,849,415 (Zweigle) disclosed the reversible diffusion of active organic agents into an aqueous dispersion of water-insoluble cellulose ether. The dispersion would be capable of spray application and act as a sustained release mechanism for the active ingredient, as the agent reverses its affinity for the cellulose ether. Among the suggested active agents was chlorpyrifos, which could advantageously be sprayed as an insecticide directly onto the thatch covering a field. This approach did not consider the synergy of cellulose and chlorpyrifos as a termiticide, however, or recognize the efficacy of such a combination for long term, low concentration, protection against termites.

Thus, it is an object of the invention to provide a termite control mixture that includes a poison mixed with a food source that may be applied uniformly across an area of property. It is a further object to provide a mixture of termiticide and food that may be applied using the same equipment and techniques employed by pest control operators to administer standard termiticidal compounds. It is a further object to distribute the mixture in the ground to form a continuous barrier between subterranean termites and the structure to be protected. It is another object to enhance the effectiveness of a given amount of poison by inducing termites to ingest poisoned food and return with it to the nest, poisoning other termites and the queen. It is yet another object of the invention to afford termite protection and control using a smaller amount of potentially harmful poison than is necessary with standard termiticides.

SUMMARY OF THE INVENTION

The present invention provides a way to continue the easy application of an unbroken termiticide barrier while also taking advantage of the enhanced effectiveness offered by termite baiting techniques. A soluble, polymer form of cellulose, such as methyl cellulose or another of the cellulose ethers, is combined with very low concentrations of an approved liquid termiticide, such as chlorpyrifos. The viscosity of the cellulose ether is controllable, and may be set so that the mixture can be broadcast with the conventional pressure spray applicators used in the pest control industry. Thus, the identical termiticide barrier formation procedures may be used to apply much lower concentrations of approved chemicals than before, but mixed with a source of food sought by termites. Termites encountering the barrier will ingest the poisoned cellulose and return to the colony to share the toxic food.

DETAILED DESCRIPTION OF THE INVENTION

The invention is a liquid, sprayable mixture of termiticide and a cellulose source, capable of being applied to soil as a barrier in the same manner as conventional termiticides are currently broadcast. The mixture's viscosity must allow it to flow through a conventional pressure spray applicator, and it must penetrate and hold in soil to a depth of about 1–2 inches (2.5–5 cm), approximately the same as liquid termiticides in prescribed concentrations. Commercially available, EPA-approved termiticides form the poison component of the mixture. Some such termiticides are available only to licensed pest control operators, while others may be available for home use.

The liquid cellulose component of the mixture may be readily obtained from commercial sources. Ingestible, nearly pure cellulose is available in water soluble polymer form as a cellulose ether. One of the cellulose ethers, methyl cellulose, has been widely used in foods, pharmaceuticals, personal care products, and coatings for over 50 years. Methyl cellulose is available in varying grades of purity up to those approved for human consumption and in a wide range of viscosities.

Other forms of cellulose, or cellulose ethers, for example CMC, HEC, HPC, HEMC, HPMC, ethyl cellulose or HEEC, may be used in the invention. The important characteristics are that the mixture include cellulose, the primary food source for termites, and that the mixture of termiticide and cellulose have a liquid form (which may include colloidal or other suspensions) that can be dispensed through a sprayer or applicator similar to those used in the pest control industry. In like manner, the termiticide component may be any effective termite poison dispensable as a liquid, including the now-banned chlorinated hydrocarbons.

Although the scope of the invention encompasses various combinations of termiticides and cellulose the experimentation performed and the detailed description below is focused on a particular formulation of the invention, namely, a mixture of methyl cellulose and a liquid chlorpyrifos. Methyl cellulose is widely available, particularly from Dow Chemical Company. Chlorpyrifos, a broad spectrum insecticide, is sold under the names DURSBAN, BRODAN, DETMOL UA, ERADEX, LORSBAN, PIRIDANE, STIPEND and CHLORPYRIFOS PRO. The methyl cellulose used in experiments was a form commonly used in the motion picture industry for creating special-effects (particularly the appearance of bleeding wounds) and as a non-toxic adhesive or fixative. When purchased as a liquid it is known as "studio paste" and when purchased for the latter use, it is available in a powder known as "cellulose adhesive." Subsequent experimentation determined that powdered hydroxyethyl cellulose is effective.

EXAMPLE 1

Testing was undertaken to ascertain the efficacy of the inventive compound using low concentrations of chlorpyrifos. A 5×5 grid was established to check 25 cells in a location with typical desert soil. Each cell contained four concrete blocks wired together so that they enclosed an area of approximately one square foot. A fifth concrete block was used as a cap to protect the plot from the elements after treatment. As soon as the treatment had dried, a roll of toilet paper was set vertically in the center of the treated soil in each enclosure, after which the concrete lid was put in place.

Test treatments were set using a location spread of five repetitions of a control and four different formulations. The control cells were treated with water. Termiticide formulations for active test cells were made with Dursban TC, a commercially available professional grade of chlorpyrifos manufactured by Dow Elanco. Like other commercial termiticides, Dursban TC concentrate contains less than half (42.8%) active ingredient by volume, with the remainder constituting inert materials. Thus, a formulation of one gallon of Dursban TC in 100 gallons of water results in a concentration of 0.5% chlorpyrifos.

The tested concentrations were 0.75% chlorpyrifos and 0.5% chlorpyrifos (the minimum concentration recommended for Dursban TC), 0.5% plus cellulose and 0.25% plus cellulose. Treatment rates and volumes were calculated to match current EPA label directions for a horizontal preconstruction barrier treatment: one gallon of emulsion per 10 linear feet. Treatments were applied with a sprinkling can to the test plots.

The effectiveness of treatments was determined by visual inspections at three month intervals. The concrete lids were removed. Then the toilet paper rolls were picked up, examined for evidence of termites and/or termite damage, and replaced. The following table gives the number of infested plots after application.

TABLE 1

Infested Plots Over Time

| | Water | Dursban 0.75 | Dursban 0.5 | Dursban 0.5 + Cellulose | Dursban 0.25 + Cellulose |
|---|---|---|---|---|---|
| 3 months | 5 | 0 | 0 | 0 | 0 |
| 6 months | 5 | 0 | 3 | 0 | 0 |
| 9 months | 5 | 0 | 5 | 0 | 0 |
| 12 months | 5 | 3 | 5 | 0 | 0 |

The infestation of all control plots within three months demonstrated that the toilet paper rolls were an appropriate way to measure infestation and that the experiment was conducted in an area with adequate termite pressure. The results with the conventional treatment showed termite infestation within six months at the lower concentrations, and within one year at the higher concentration. This is consistent with a time degradation in effectiveness. The results with a cellulose additive show that the barrier remained effective even when lower concentrations of poison were present.

Environmental Protection Agency regulations promulgated in June, 2000 reduced the maximum allowed application concentration of chlorpyrifos for pre-construction ground treatment to 0.5%, a substantial reduction from the maximum 4% concentration previously allowed. As demonstrated in example 1, Dursban TC at such a low concentration loses effectiveness as a termite barrier in a matter of months. Similar results are experienced with such low concentrations of other commercial termiticides. Consequently, use of the invertive mixture may constitute the only way to obtain acceptable termite protection with chlorpyrifos-based termiticides.

The other most common class of standard commercial termiticide compounds is pyrethroids, which are synthetic derivatives of pyrethrins, natural insecticides produced by certain species of the chrysanthemum plant. Pyrethroids inhibit nervous system function in termites, though differently from the cholinesterase inhibitors such as organophosphates. The effect can be triggered either by contact or by ingesting the substance. Pyrethroids also exhibit a repellency effect on termites, inducing foraging workers to avoid treated areas.

The pyrethroids commonly used as termiticide are permethrin, cypermethrin and fenvalerate. An experiment using a commercial permethrin product was undertaken to determine effectiveness of the cellulose additive to enhance performance at low concentrations of poison.

EXAMPLE 2

As with Example 1, a 5×5 grid was established to check 25 cells in a location with typical desert soil. Each cell was set up with concrete blocks and a roll of toilet paper. Five repetitions of five formulations, including water as a control, were laid out.

Termiticide formulations for active test cells were made with Dragnet FT, a commercially available professional grade of permethrin manufactured by FMC Corporation. Dragnet FT is formulated so that 36.8% of the packaged product is active ingredient, and the product is labeled for use at active concentrations of 0.5% to 2.0%, with 0.5% the recommended concentration for pre-construction barrier establishment. The tested concentrations were 0.25% permethrin and 0.125% permethrin, 0.125% permethrin plus cellulose and 0.06% permethrin plus cellulose. Treatment rates and volume were calculated to match current EPA label directions for a horizontal preconstruction barrier treatment: one gallon of emulsion per 10 linear feet. Treatments were applied with a sprinkling can to the test plots.

The effectiveness of treatments was determined by visual inspections at three month intervals, as in Example 1. The following table gives the number of infested plots after application:

TABLE 2

Infested Plots Over Time

| | Water | Dragnet 0.25 | Dragnet .125 | Dragnet .125 + Cellulose | Dragnet 0.06 + Cellulose |
|---|---|---|---|---|---|
| 3 months | 4 | 0 | 0 | 0 | 0 |
| 6 months | 5 | 0 | 2 | 0 | 0 |
| 9 months | 5 | 1 | 4 | 0 | 0 |
| 12 months | 5 | 3 | 4 | 0 | 0 |

The infestation of all control plots within three months demonstrated that the toilet paper rolls were an appropriate way to measure infestation and that the experiment was conducted in an area with adequate termite pressure. The results with the conventional treatment showed termite infestation within six months at the lower concentration and within one year at the higher concentration. This is consistent with a time degradation in effectiveness. The results with a cellulose additive show that the barrier remained effective even when lower concentrations of poison were present.

The commercially available pyrethroids and their recommended concentrations for termite pretreatment are Tribute, a fenvalerate made by AgrEvo (0.5% to 1.0%), Demon TC, a cypermethrin made by Zeneca Inc. (0.25% to 0.5%), Prelude, a permethrin made by Zeneca Inc. (0.5% to 1.0%) and Dragnet FT as referenced above. All of these compounds, which depend in part on contact or ingestion by the termite for killing ability, will benefit from combination with a cellulose additive to attract foraging termites into ingesting the poison. It is reasonable to infer that the additive will permit reducing the in-ground concentration to one-half or less of the recommended concentration for the un-enhanced product.

Preliminary testing has been undertaken to confirm the efficacy of the cellulose additive with any of the newer commercial termiticide poisons, including bifenthrin, isophenphos, fipronil, imidacloprid and phenyl pyrazol. All of these also depend in part on contact for effectiveness in killing termites, and all would work better if the termite were induced to ingest them. Consequently, substantially reduced concentrations may be expected to have the same effect as the standard concentrations when the cellulose additive is included.

Although the present invention has been described in considerable detail with reference to certain preferred versions thereof, other versions are possible. For example, a variety of liquid cellulose sources and termite poisons may be employed in the mixture. Some forms of cellulose source, particularly methyl cellulose, may be sufficiently soluble so that the invention mixture may be prepared and stored in containers to be mixed later with water before use. Other forms, such as some powdered forms, are better kept separate from the termiticide concentrate and added to the applicator tank immediately before broadcasting the mixture. Therefore, the spirit and scope of the appended claims should not be limited to the description of the preferred versions contained herein.

What is claimed is:

1. A method of pretreating soil beneath a foundation of a future structure so as to protect the structure against termite infestation comprising the steps of preparing a standard termiticide composition by adding a pyrethroid poison to a prescribed volume of water to achieve a concentration of 0.06 to 0.125 percent poison, adding a cellulose source which when combined with the termiticide composition forms an enhanced liquid composition having a viscosity low enough to permit flow through a pump sprayer, and spraying the enhanced composition on an area of soil beneath and around a location where the foundation is to be placed so as to form a continuous barrier between the future structure and any subterranean termites in the vicinity.

2. The method of claim 1 wherein the pyrethroid poison is a fenvalerate.

3. The method of claim 1 wherein the pyrethroid poison is a cypermethrin.

4. The method of claim 1 wherein the pyrethroid poison is a permethrin.

5. The method of claim 1 wherein the cellulose source is a liquid, powdered or granulated form of methyl cellulose.

6. The method of claim 1 wherein the cellulose source is a liquid, powdered or granulated form of methyl cellulose.

7. The method of claim 1 wherein the cellulose source is powdered hydroxyethyl cellulose.

8. A method of treating live termite infestation of a structure comprising the steps of preparing a standard termiticide composition by adding a pyrethroid poison to a prescribed volume of water to achieve a concentration of 0.06 to 0.125 percent poison, adding a cellulose source that when combined with the termiticide composition forms an enhanced liquid composition having a viscosity low enough to permit flow through a pump sprayer, and spraying the enhanced composition on and near the location where any infestation is observed.

9. The method of claim 8 wherein the cellulose source is a liquid, powdered or granulated form of a cellulose ether.

10. The method of claim 8 wherein the cellulose source is a liquid, powdered or granulated form of methyl cellulose.

11. The method of claim 8 wherein the cellulose source is powdered hydroxyethyl cellulose.

* * * * *